United States Patent [19]

Klemm

[11] Patent Number: Plant 7,199

[45] Date of Patent: Mar. 20, 1990

[54] GERANIUM NAMED MANEPERT

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 244,312

[22] Filed: Sep. 15, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinctive geranium plant variety particularly distinguished by its very floriferous growth habit and its profuse production of bright Carmine Rose-colored flowers comprising relatively small clusters borne on relatively long, downwardly hanging branches standing over a background of glossy, dark green, medium sized leaves which provide a brilliant background for the flowers. The florets are of medium size and well filled and seven or eight of them form a round cluster, a plurality of which are carried on the hanging branches extending from upright stalks that are about 12 to 13 cm. long. The flowers are very double and appear somewhat like roses when they open and the flower clusters nearly cover the hanging tendrils which can grow in length up to about 50 cm.

1 Drawing Sheet

BACKGROUND OF THE NEW PLANT

My new geranium cultivar originated as a seedling of a hybrid produced by my crossing the variety 'Pink Charme' (unpatented) with the pollen of the variety 'Tavira' (unpatented) in 1984 at my nursery in Stuttgart, West Germany. This seedling bloomed for the first time in 1985 and because of the outstanding nature of the plant, it was selected for reproduction, which was done by me and under my direction at Stuttgart by means of cuttings. This propagation was carried on through several successive generations which demonstrated conclusively that the distinctive characteristics of this plant would remain true from generation to generation and appeared to be firmly fixed.

DESCRIPTION OF THE DRAWING

My new geranium cultivar is illustrated by the accompanying photographic drawing, which shows a fully developed cluster of florets which illustrates their form and their light Carmine Rose coloring, the colors being as nearly true to that herein specified as is reasonably possible to obtain by conventional photographic procedures.

DESCRIPTION OF THE NEW PLANT

The following is a detailed description of my new geranium variety as observed of plants grown both in greenhouse and outdoors at Stuttgart, with the color designation being according to The R.H.S. Colour Chart published by The Royal Horticultural Society of London, England.

THE PLANT

Origin: Seedling.

Parentage:

*Seed parent.*—'Pink Charme' (unpatented).

*Pollen parent.*—'Tavira' (unpatented).

Classification:

*Botanic.*—*Pelargonium peltatium* Hybrid.

Commercial.—Geranium.

Form: A hanging plant with long branches.

Main stem length: Up to 50 cm. or more during one season.

Branching character: Very little branching.

Growth: Vigorous with good strength.

Growth rate: Rapid.

Foliage:

*Quantity.*—Medium.

*Size of leaf.*—About 7 cm. long and 6 cm. wide.

*Leaf shape.* Ivy-shaped with entire margins.

*Aspect.*—Glossy.

*Color.*—Upper side — Dark Green with very weak zonation. Under side — Light Green.

*Ribs and veins.*—The leaf has five main veins.

THE BUD

Size: Small.

*Diameter.*—About 10 mm.

*Length.*—About 17 mm.

Form: Globular.

Color of florets: When sepals first divide, When petals beging to unfurl, light pink.

Sepals:

*Shape.*—Long and pointed. The sepals stand up when the flowers open.

*Color.*—Green.

Calyx:

*Shape.*—Flat and wide open.

*Spreading.*—The sepal does not spread.

*Aspect.*—Hairy.

THE INFLORESCENCE

Blooming habit: Continuous and profusely from Spring to late Fall.

Cluster:

*Size.*—Medium. Diameter — About 8 to 9 cm.

*Number of florets in cluster.*—About 6 or 7.

Florets:

*Size.*—Medium.

*Shape.*—When bloom first opens, cup-shaped. When bloom matures, flat.

Petalage:

*Form.*—Broadly obovate with entire margins.

*Arrangement.*—Imbricated.
*Texture.*—Soft.
*Appearance.*—Shiny.
*Color.*—Carmine Rose RHS 52-C.

Petaloids:
*Number.*—5 to 10.
*Size.*—About 8 to 12 mm.
*Color.*—Carmine Rose

Persistence: The petals stay on the flower stem about fourteen days.

Lasting quality: Very good.

THE REPRODUCTIVE ORGANS

Stamens:
*Number.*—3 or 4.
*Arrangement.*—Various.
*Anthers.*—Size: Small; about 1.5 mm. Color: Yellow.
*Filaments.*—Length: About 2 to 3 mm. Color: White.
*Pollen.*—Color: Yellow.

Pistil:
*Number.*—One or none.

*Style.*—Length: About 2 mm. Color: Green.
*Stigma.*—Character: 3 to 5 parts. Color: White.

Ovaries: Small and sometimes abnormally grown.

THE FRUIT

Fertility: Nearly sterile.
Shape: Ovoid.
Color at maturity: Brown.

This clear-salmon flowering ivy sometimes starts a little later than others but it is very floriferous and the long, downward hanging branches are covered by the relatively small flower clusters. The color is very impressive with the background of the glossy, dark green leaves. The flowers are very double and look a bit like roses when they open.

I claim:

1. The new and distinctive geranium variety, substantially as herein shown and described, characterized by its downwardly hanging branches bearing many lengthwise-distributed flower clusters of a light pink coloring and by its glossy, dark green foliage.

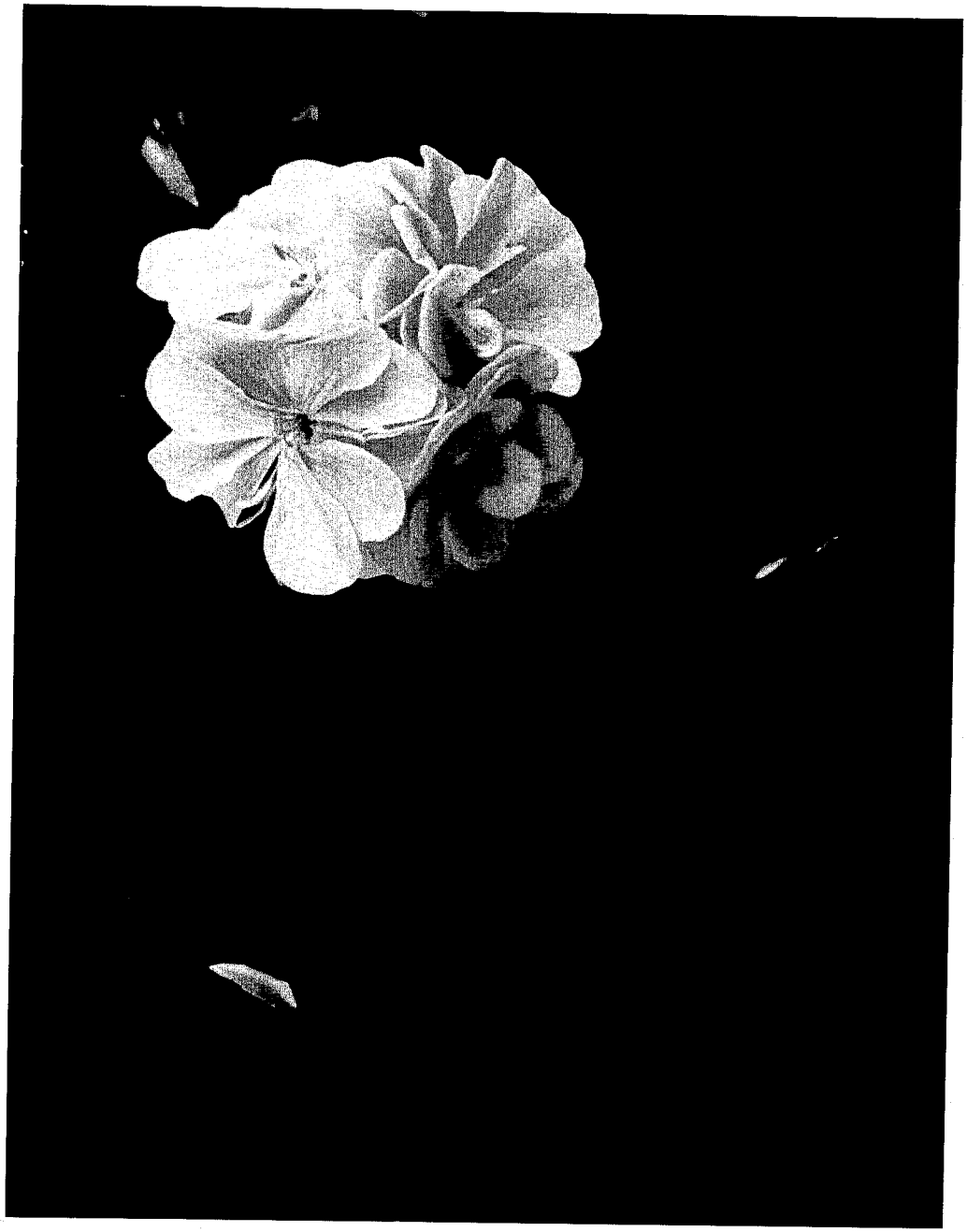

* * * * *